(12) United States Patent
Kageyama et al.

(10) Patent No.: US 7,019,821 B2
(45) Date of Patent: Mar. 28, 2006

(54) METHOD AND APPARATUS FOR DETECTING BLOOD IN SHELL EGGS

(75) Inventors: Takuo Kageyama, Tsuyama (JP); Hayashi Kondo, Tsuyama (JP); Masao Uetsuki, Tsuyama (JP); Naoki Inamoto, Kumamoto (JP)

(73) Assignee: Kyowa Machinery Co., Ltd., Okayama (JP)

( * ) Notice: Subject to any disclaimer, the term of this patent is extended or adjusted under 35 U.S.C. 154(b) by 0 days.

(21) Appl. No.: 10/357,407

(22) Filed: Feb. 4, 2003

(65) Prior Publication Data

US 2003/0156273 A1  Aug. 21, 2003

(30) Foreign Application Priority Data

Feb. 8, 2002  (JP) .............................. 2002-031669

(51) Int. Cl.
*A01K 43/00* (2006.01)

(52) U.S. Cl. .......................................... 356/53; 356/52

(58) Field of Classification Search .................. 356/52, 356/53, 55, 56, 57, 58; 209/509, 510, 511, 209/512, 513, 514, 515
See application file for complete search history.

(56) References Cited

U.S. PATENT DOCUMENTS

| | | | |
|---|---|---|---|
| 2,823,800 A | | 2/1958 | Bliss |
| 3,740,144 A | * | 6/1973 | Walker .......................... 356/53 |
| 4,039,259 A | * | 8/1977 | Saito et al. .................... 356/53 |
| 4,063,822 A | * | 12/1977 | deJong et al. ................. 356/53 |
| 4,161,366 A | * | 7/1979 | Bol et al. ....................... 356/56 |
| 4,182,571 A | * | 1/1980 | Furuta et al. .................. 356/53 |
| 4,805,778 A | * | 2/1989 | Nambu ........................ 209/510 |
| 4,820,045 A | * | 4/1989 | Boisde et al. ............... 356/319 |
| 5,615,777 A | * | 4/1997 | Weichman et al. ......... 209/511 |

(Continued)

FOREIGN PATENT DOCUMENTS

JP  51-48995  12/1976

(Continued)

OTHER PUBLICATIONS

Patent Abstracts of Japan, Publication No. 05-046731; Feb. 26, 1993; Iseki & Co., LTD.

(Continued)

*Primary Examiner*—Layla G. Lauchman
*Assistant Examiner*—Juan D. Valentin, II
(74) *Attorney, Agent, or Firm*—Sughrue Mion, PLLC

(57) ABSTRACT

An egg inspecting apparatus (1) of the present invention includes an optical path switching and projecting assembly (30) for automatically selecting one of a plurality of optical paths through which a white source light (11) emitted from a light source (2) is guided and also for sequentially projecting the white source light (11) from the associated optical paths onto eggs held at respective positions, a spectrum converting assembly for spectrally analyzing light which has been transmitted through each of the eggs and converting it into a spectrum, and a determining circuit (5) for determining whether the egg is a normal egg or a bloody egg by using the spectrum so converted. By way of example, a spectrum of an egg is measured and a secondary differential curve is formulated for classification of the eggs according to egg shell colors. By comparing a spectral pattern of the transmitted light of the egg with that of a normal egg for each of the shell colors, and assaying a pattern similarity by means of a correlational assay method, whether the egg is a normal egg or a bloody egg can be determined.

16 Claims, 5 Drawing Sheets

U.S. PATENT DOCUMENTS

| | | | |
|---|---|---|---|
| 6,234,320 B1 * | 5/2001 | Hebrank | 209/510 |
| 6,504,603 B1 * | 1/2003 | Schouenborg | 356/53 |
| 2002/0075476 A1 * | 6/2002 | Chalker et al. | 356/53 |

FOREIGN PATENT DOCUMENTS

| | | |
|---|---|---|
| JP | 06-043093 | 2/1994 |
| JP | 2002-153160 | 5/2002 |
| WO | WO 99/01762 | 1/1999 |

OTHER PUBLICATIONS

Patent Abstracts of Japan, Publication No. 2000-241347; Sep. 8, 2000; Kubota Corp.

Patent Abstracts of Japan, Publication No. 06-241988; Sep. 2, 1994; Kubota Corp.

Patent Abstracts of Japan, Publication No. 07-153810; Jun. 16, 1995; Fujitsu Ltd.

Patent Abstracts of Japan, Publication No. 03-026941; Feb. 5, 1991; Japan Spectrocopic Co.

Patent Abstracts of Japan, Publication No. 04-194650; Jul. 14, 1992; Matsushita Electric Works.

Patent Abstracts of Japan, Publication No. 04-140618; May 14, 1992; Kubota Corp.

\* cited by examiner

METHOD AND APPARATUS FOR DETECTING BLOOD IN SHELL EGGS

BACKGROUND OF THE INVENTION

1. Field of the Invention

The present invention relates to an egg inspecting apparatus, for detecting blood in shell eggs, used at an inspecting station of an egg grading and packaging system for automatically and non-destructively inspecting eggs to find blood in shell eggs known to the trade as "bloods" in which blood is spotted on the yolk surface of an egg or distributed on the white of an egg. The present invention also relates to a method of inspecting the eggs and an egg grading and packaging system utilizing the egg inspecting apparatus to perform the egg inspecting method.

2. Description of the Prior Art

According to USDA Agricultural Statistics in 1991, egg production in 1990 was 553 billions in the world, including 159 billions in China, 82 billions in USSR and 68 billions in the United States. In Japan, about 40 billion hen's eggs (about 2.5 million tons) are produced each year and about 70% (about 28 billion eggs) of them is packaged with one pack containing 10 eggs on average. To provide egg packs each containing 10 eggs, an egg grading and packaging system having a capability of handling some ten thousands of eggs to a fraction of one million eggs per hour is largely employed. In this egg grading and packaging process, only normal eggs are necessarily packaged while defective eggs such as bloody eggs having their yolk surface spotted with blood or having blood distributed on their white, dirty eggs having fowl droppings on an outer surface thereof and cracked eggs have to be rejected unmistakenly.

Hitherto, an egg inspecting method to determine if an egg is a bloody egg is largely practiced, in which eggs are generally inspected by observing the coloring of each of the eggs with naked eyes from above while the eggs are illuminated by a beam of light projected from below onto each of the eggs within a dark room. However, this known method requires an inspector to be well skilled and, accordingly, depending on the degree of skill and fatigue suffered by the inspector, the accuracy of inspecting results and the reproducibility tend to fluctuate. Also, with the known egg inspecting method, there is an additional problem in that so far as colored eggs having a rose-pink or brown shell are concerned, such eggs cannot help but being shipped without being sufficiently inspected because of a partial overlapping between absorption wavelength regions exhibited respectively by hemoglobin (a blood component) and protoporphyrin which is a pigment of an egg shell. In view of this, various optical egg inspecting methods including an optical type have been suggested in and practiced by, for example, U.S. Pat. No. 2,823,800 and the Japanese Patent Publication No. 51-48,995.

On the other hand, in the conventional egg grading and packaging system, the eggs are transported in a plurality of rows (six rows in most cases) by means of associated transport rollers past stations such as cleansing, drying, aligning, inspecting and weighing stations and are then transferred onto a single row of associated transport rollers that transport the eggs to a packaging station where after the total weight has been adjusted uniformly, the eggs can be packaged. However, when the eggs having been transported by multi-row transport rollers are transferred onto single row transport rollers, the transport speed increases in inverse proportion to a factor of reduction in number of the rows (for example, six folds in the case where the eggs having been transported by six-row transport rollers are transferred onto single row transport rollers) and, accordingly, where it is desired to increase the handling efficiency by utilization of a system in which the transport speed with the multi-row transport rollers is increased to the permissible uppermost limit at which breakage of some of the eggs being transported will not occur, it is dangerous for the eggs to be transferred onto the single row transport rollers.

While requirements to reduce the egg handling time, that is, to increase the egg transport speed are currently increasing, a technique has been developed to efficiently package eggs while the latter are transported by a multi-row transport system without the eggs being transferred onto the single row transport rollers from the multi-row transport rollers, such as disclosed in, for example, the Japanese Laid-open Patent Publication No. 2002-153,160. Accordingly, it is desirable that the egg inspection also be performed efficiently and highly accurately while the eggs are transported by the multi-row transport system. By way of example, an egg inspecting method such as suggested in the Japanese Laid-open Patent Publication No. 6-43,093 appears to be effective in performing the egg inspection at a site preceding a packaging process in a single row transport system. However, in terms of performance and cost, an effective egg inspecting method has not yet been developed which suits to the high speed multi-row transport system.

As discussed hereinabove, the optical egg inspecting method has made it possible for the bloody eggs to be inspected with relatively high accuracy so long as the egg shell is white-colored. However, when it comes to the colored eggs such as having rose-pink or brown egg shells, the accuracy of inspection is considerably low and the practicability is also low because the absorption wavelength exhibited by hemoglobins contained in the bloody eggs and that exhibited by protoporphyrin, which is a pigment of the egg shell, overlap partially with each other. Thus, problems inherent in the conventional optical egg inspecting method may be summarized as associated with establishment of technologies on (1) wavelength distribution and brightness of a source light, (2) qualitative classification of the egg shell colors, (3) systematic utilization of a diversity of spectral information. Also, with respect to the egg inspection as well as the egg packaging, (4) development of a method that can be used in the high speed multi-row transport system is desired.

SUMMARY OF THE INVENTION

The problem associated with (1) wavelength distribution and brightness of a source light can be solved when a new and powerful halogen lamp is employed for emitting a white light of high brightness. The problem associated with (2) qualitative classification of the egg shell colors is solved by the provision of a system in which by taking it into consideration that "the egg shell color can be determined only by a concentration of protoporphyrin" according to L. Schwarz, W. Deckert and H. Ketels, Z. Physiol. Chem., Bd. 312, 37–44 (1958), the egg shell colors are classified according to the waveform at the absorption wavelength region of protoporphyrin. The problem associated with (3) systematic utilization of a diversity of spectral information can be solved by the provision of a system in which the similarity between the respective spectral patterns exhibited by a hen's egg and a normal egg is assayed for each egg shell color, for example, by the use of a correlation coefficient at the absorption wavelength region of the hemoglobin that is inevitably contained in the bloody egg. The problem associated with (4) development of the method that can be used in the high speed multi-row transport system can be solved by developing an automatic optical path selector capable of guiding a white source light selectively into one of a plurality of optical paths at a high speed with the use of a system in which, for example, a plane mirror is caused to undergo an angular movement by means of a rotation control motor while in synchronism with operation of the multi-row transport rollers. So far as (4) is concerned, although the provision of the light source for each of the plural optical paths would result in increase of the size of equipment and, on the other hand, the use of the single source light to illuminate the plural optical paths simultaneously would result in reduction in brightness, the present invention makes use of a system in which the single source light is sequentially guided into one of the plural optical paths and, accordingly, it is possible to secure a high brightness while the equipment can be reduced in size.

Also, instead of the angular movement of the plane mirror, the automatic optical path selector can be driven by various means such as an angular movement or rotation of an optical head coupled with a flexible optical fiber, rotation of a polygon mirror, and others.

In the practice of the present invention, in the first place, spectra of normal eggs are measured and recorded for each egg shell color. Then, after the measurement of a spectrum of a hen's egg, the spectrum is normalized by the light absorbancy at the wavelength of 685 nm of light little absorbed by a component of the respective egg, followed by classification of the egg shell colors at an extreme absorbancy of the shell pigment at a wavelength band of 640 to 650 nm. Thereafter, at the spectral absorption region of 560 to 590 nm exhibited by a blood, the similarity between the spectral pattern of the egg and that of a normal egg that has been recorded for each shell color is assayed by any of various pattern recognition techniques, for example, a correlation coefficient according to the correlational analyzing method to thereby determine if the egg inspected is a bloody egg or not for each of classified egg shell colors. In this egg inspecting method, the coefficient of correlation between the spectral patterns does not change even if such spectrum is normalized. While, to determine the bloody egg, the spectrum of the transmitted light through the egg can be suitably used, the spectrum of any of the transmitted light through the egg and the light reflected from the egg shell surface can be suitably employed to classify the egg shell colors.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Before the description of preferred embodiments of the present invention proceeds, it is to be noted that in view of the fact that most of the egg grading and packaging systems now in use are of a design in which a multi-row transport mechanism of a specification including six parallel conveyors is employed, the present invention will be described in detail with reference to the accompanying drawings as applied to one of those egg grading and packaging systems. More specifically, the multi-row transport mechanism used in this type of the egg grading and packaging system is so designed as to transport eggs to be illuminated. in six rows with each transverse line of six eggs being aligned with each other in a direction perpendicular to the direction of transport.

Figure 1:
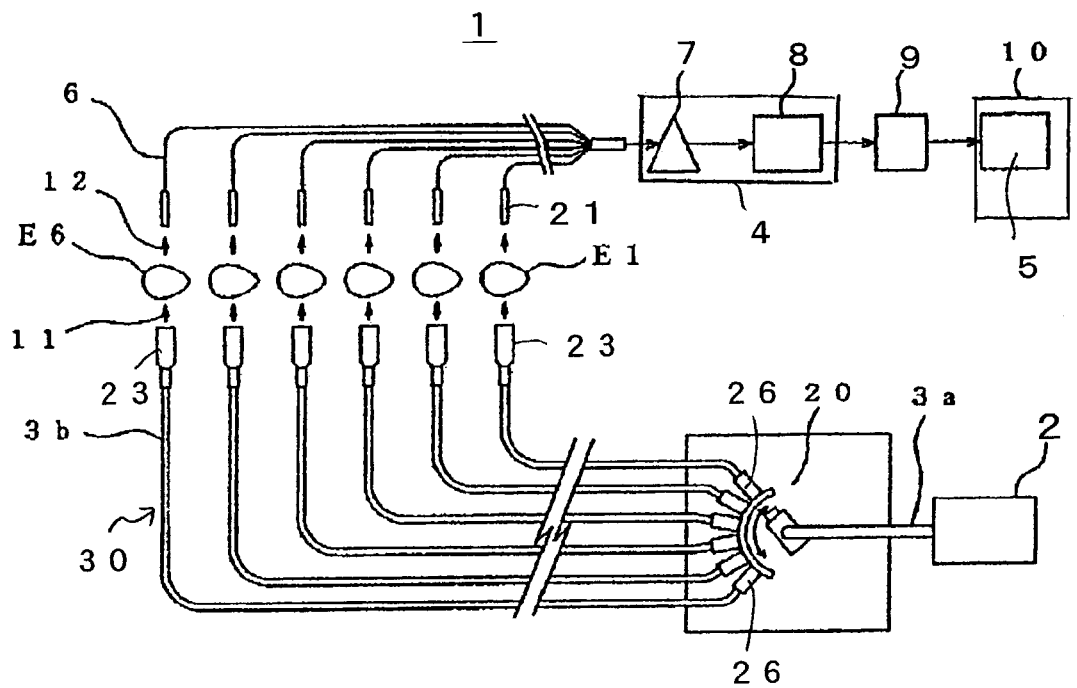
FIG. 1 is a schematic diagram showing an egg inspecting apparatus according to a preferred embodiment of the present invention.

Referring first to FIG. 1, there is shown a basic structure of an egg inspecting apparatus according to a first preferred embodiment of the present invention. The egg inspecting apparatus 1 of a type capable of being operatively associated with a transport mechanism such as a six-row roller conveyor mechanism includes an optical path switching and projecting assembly 30 having a light source 2 such as a halogen lamp of a kind capable of emitting a white source light 11, an automatic optical path selector 20 for sequentially directing the white source light 11 towards six eggs E1 to E6, then forming a respective transverse line, among eggs being carried in six rows, and optical beam projecting fibers 3b equal in number to the number of the eggs E1 to E6 of each transverse line for projecting the white source light 11 onto the eggs E1 to E6 one at a time.

The egg inspecting apparatus 1 also includes an analyzed spectrum converting assembly having light receivers 21 equal in number to the number of the eggs E1 to E6 of each transverse line for receiving transmitted white source light 12 which has been passed through the respective eggs E1 to E6, optical beam receiving fibers 6 for guiding the transmitted white source light 12 towards a spectral analyzing and light receiving unit 4, the spectral analyzing and light receiving unit 4 made up of a spectral analyzing element 7 for spectrally analyzing the transmitted white source light 12 and a light receiving element 8 such as a charge coupled device (CCD) for converting a light signal into an analog electric signal according to the wavelength to thereby output an analog spectrum, and an analog-to-digital (A/D) converter 9 for converting the analog spectrum into a digital spectrum. The egg inspecting apparatus 1 furthermore includes an arithmetic unit 10 including a determining circuit 5 for performing an arithmetic process on the converted digital spectrum to determine if the egg having been inspected is one of bloods, i.e., eggs having one or more blood spots.

An optical fiber has such a property that the flexibility of the optical fiber decreases if the fiber diameter is increased to thereby increase the light receiving capability, but the light receiving capability decreases if the fiber diameter is decreased to thereby increase the flexibility of the optical fiber. In order for the optical fiber to cope with a trade-off between the flexibility and the light receiving capability, in the egg inspecting apparatus 1 embodying the present invention, an optical projecting fiber 3a is employed in the form of a bundle of 34,230 optical fiber strands of 50 μm in diameter; each of the optical projecting fibers 3b is employed in the form of a bundle of 12,390 optical fiber strands of 50 μm in diameter; and each of the optical receiving fibers 6 is employed in the form of a bundle of 15 optical fiber strands of 200 μm in diameter. Utilization of the specific optical fiber bundles for the optical fibers 3a, 3b and 6 as discussed above is effective to increase the efficiency of utilization of the limited illuminating light and also to strengthen the capability of the optical fibers being laid in complicated spaces available in the egg inspecting apparatus.

Hereinafter, a method of inspecting eggs with the use of the egg inspecting apparatus 1 of the structure described above will be described.

Figure 2:
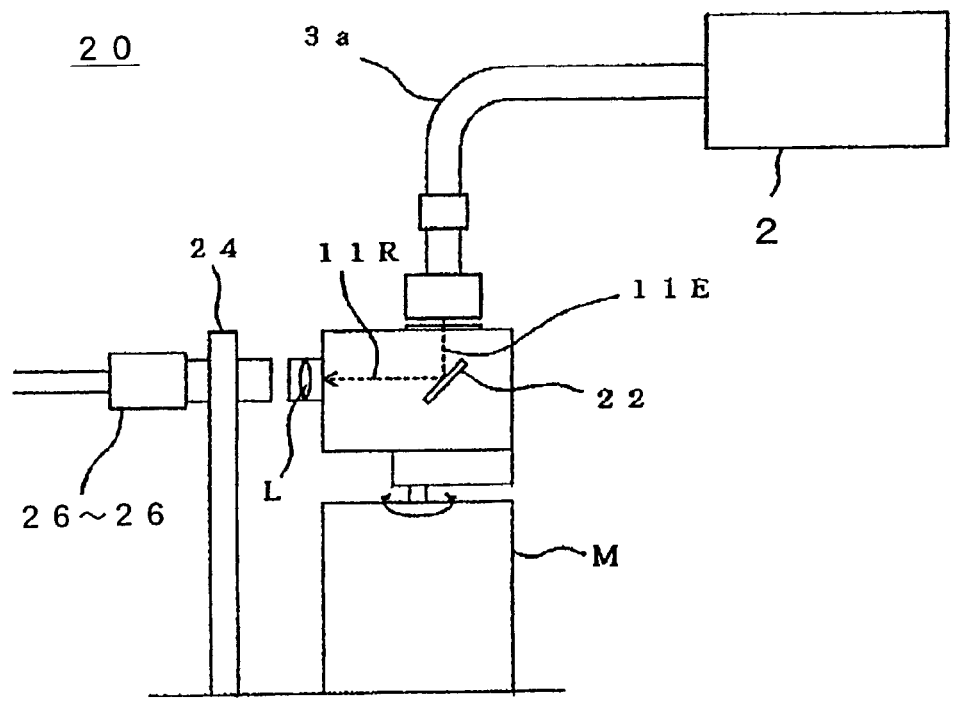
FIG. 2 is a schematic side view of the egg inspecting apparatus, showing an automatic optical path selector employed therein.

In the first place, in the automatic optical path selector 20 of the optical path switching and projecting assembly 30, the white source light 11 emitted from a single light source 2 is transmitted towards a plane mirror 22 through the optical projecting fiber 3a as shown in FIG. 2. Then, by causing the plane mirror 22 to undergo an angular movement in synchronism with operation of six-row transport rollers 70 (See FIG. 5), white light 11E is reflected towards respective light receiving ends 26~26 of the six optical projecting fibers 3b that are stationarily carried by a support plate 24. After such reflected light 11R have been received by one of the light receiving ends 26~26 and the flux of light thereof has been subsequently readjusted by a lens L, the reflected light 11R is guided to an egg inspection site through respective light projecting ends 23~23 of the optical projecting fibers 3b so that all of the eggs can be illuminated in the sequence of E1→E2→E3→E4→E5→E6→E1→E2→. . . .

Figure 3:
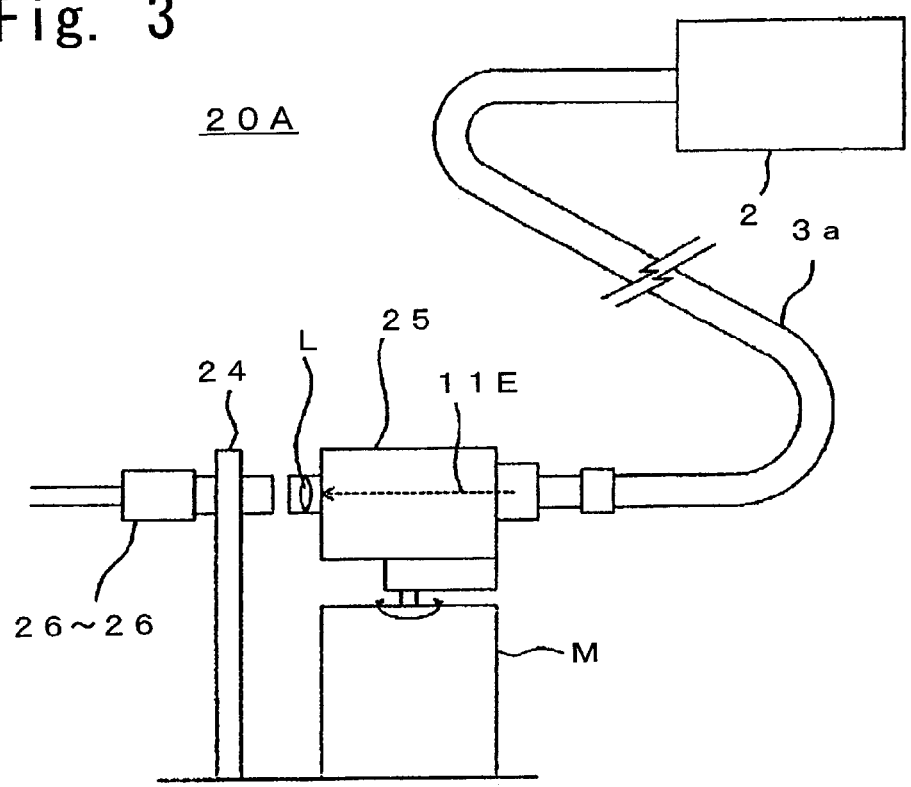
FIG. 3 is a schematic side view of the egg inspecting apparatus, showing a modified form of the automatic optical path selector employed therein.

It is to be noted that such switching of the optical paths performed by the optical path selector 20 can be achieved, in a manner similar to that described with reference to FIG. 2, even in a system wherein as shown in FIG. 3, an optical head 25 coupled with flexible optical fibers is caused to undergo an angular movement in synchronism with operation of the six-row transport rollers 70.

When the six eggs E1 to E6 of each transverse line are sequentially illuminated by the white source light 11 that is selectively transmitted by the optical path switching and projecting means 30 through the six optical paths, the source light having passed through each of the eggs is spectrally analyzed and then converted into a spectrum by the analyzed spectrum converting assembly. Then, by the determining circuit 5, after the intensity of the spectrum of light that has been transmitted through each egg has been divided by the intensity of the spectrum of the source light and the intensity has been converted into the light transmittance, the spectrum of the transmitted light is normalized by the light transmittance at the wavelength (685 nm) of light little absorbed by a component of the respective egg and, then, a secondary differential curve of the spectrum is formulated to classify the egg shell color at a peak intensity of the spectral absorption band (640 to 650 nm) exhibited by protoporphyrin which is a pigment of an egg shell. Thereafter, at the spectral absorption band (560 to 590 nm) exhibited by hemoglobins contained in a bloody egg, the similarity between the spectral pattern of the egg and that of a normal egg having no blood spots is assayed by a correlation coefficient according to the correlational analyzing method to thereby determine if the egg inspected is a bloody egg or not for each of classified egg shell colors.

It is to be noted that in order to classify the egg shell color, spectra of light reflected from an outer surface of an egg shell may be employed in place of the light having passed through the egg.

By loading into the egg inspecting apparatus 1 a computer-executable program for executing the above described egg inspecting method, bloody eggs can be automatically examined and rejected while the eggs to be inspected are successively transported.

Figure 4:
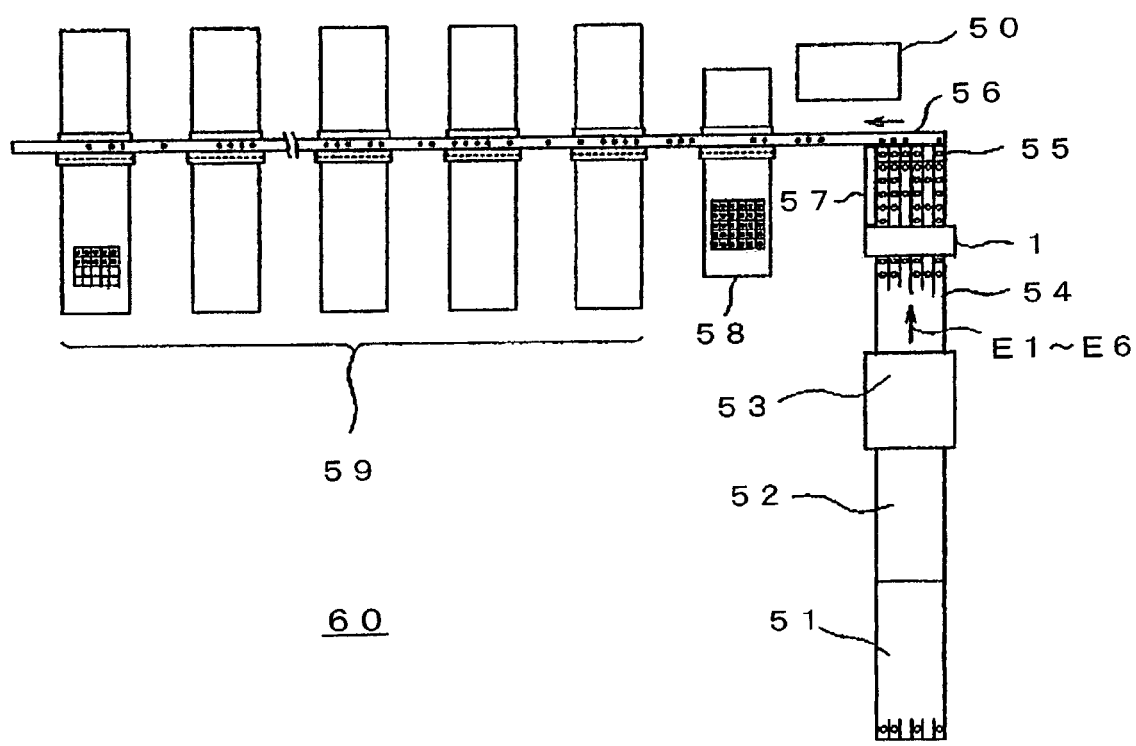
FIG. 4 is a conceptual diagram showing an automatic egg grading and packaging system employing the egg inspecting apparatus of the present invention.
Figure 5:
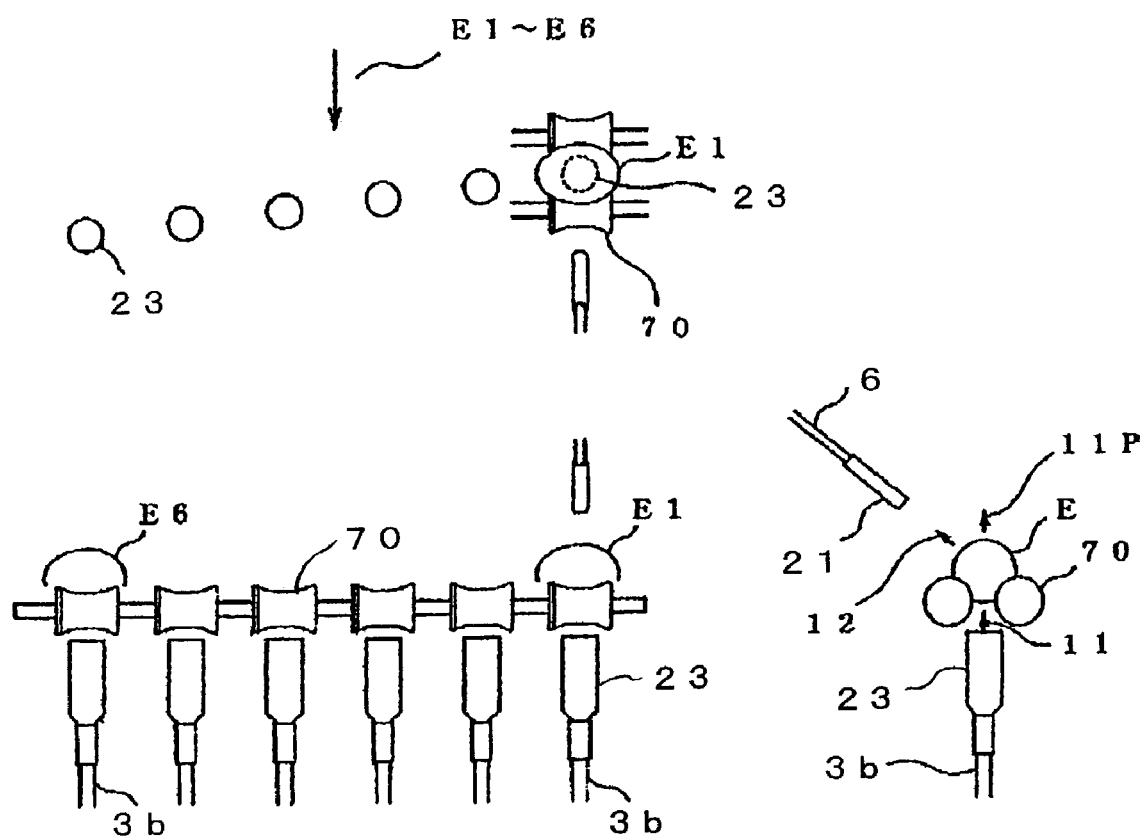
FIG. 5 is a schematic diagram showing an arrangement of optical systems in the egg inspecting apparatus of the present invention.

The egg inspecting apparatus 1 is incorporated in an egg grading and packaging system 60 as shown in a conceptual diagram in FIG. 4. This egg grading and packaging system 60 includes a system control unit 50, a cleansing unit 51, a drying unit 52, an aligning unit 53, an inspecting unit 54, a weighing unit 55, a transfer unit 56, a transport drive unit 57, a defective egg rejecting unit 58 and a packaging unit 59, with the egg inspecting apparatus 1 incorporated in the inspecting unit 54. After the eggs have been cleansed and dried by this system, a signal, indicative of one of a bloody egg and a normal egg which has been highly accurately determined by the egg inspecting apparatus 1, is supplied to the defective egg rejecting unit 58 on the basis of a command from the system control unit 50 and, accordingly, the bloody egg is rejected in a manner similar to other defective eggs. While FIG. 5 illustrates the relationship in position between the white light 11, the egg E and the transmitted light 12, if the optical projecting fibers 3b and the associated light receivers 21 are so arranged as to have their optical axes aligned with each other, the light receivers 21 can be exposed to source light 11P from the light source during the absence of the egg E on the transport roller 70 then held at the inspecting site. As a result thereof, the source light which is of a higher intensity than that of the transmitted light having passed through the egg can be supplied to the light receiving element 8, resulting in an erroneous operation. In the practice of the present invention, however, this erroneous operation is avoided by disposing the optical projecting fibers 3b relative to the respective light receivers 21 so that the optical axes of the optical projecting fibers 3b can be inclined at an angle of, for example, one or more decade angles relative to the optical axes of the light receivers 21.

Figure 6:
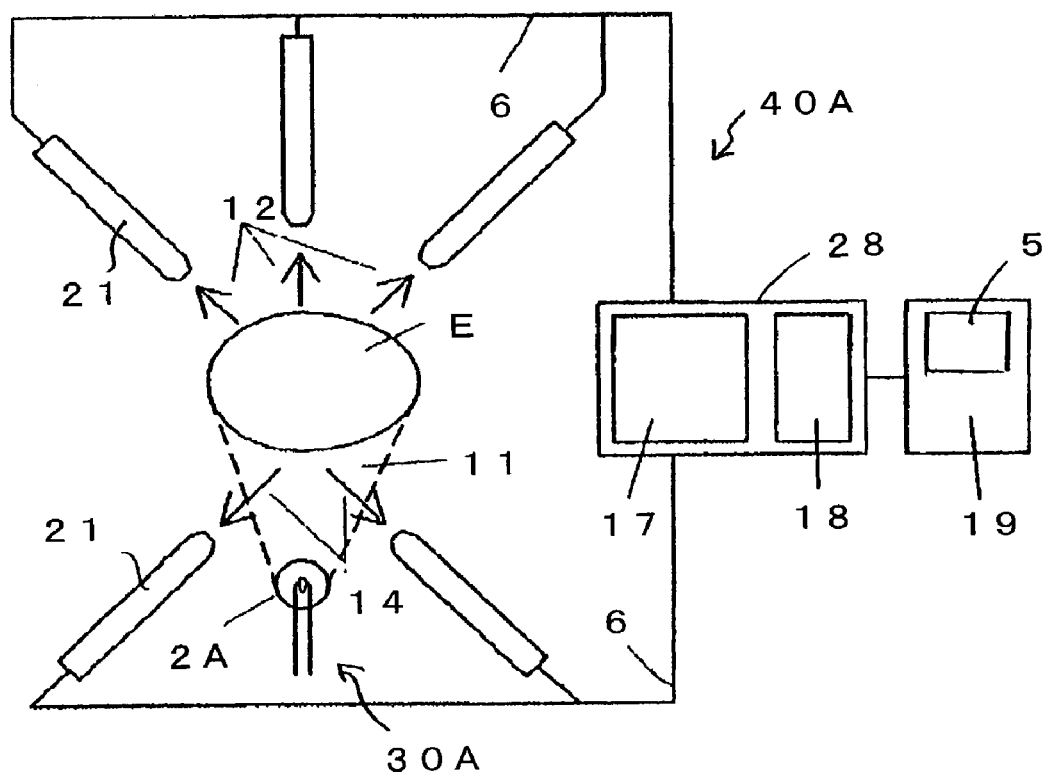
FIG. 6 is a schematic diagram showing the egg inspecting apparatus according to another preferred embodiment of the present invention.

FIG. 6 illustrates a basic structure of an egg inspecting apparatus according to a second preferred embodiment of the present invention. The egg inspecting apparatus 1A shown therein includes a projecting assembly 30A such as a halogen lamp 2A for emitting the white source light 11 to the egg E. This egg inspecting apparatus 1A also includes an analyzed spectrum converting assembly 40A having a plurality of the light receivers 21 disposed around the egg E for receiving the transmitted light 12 having passed through the egg E or light 14 having been reflected from an outer surface of the egg shell, the optical fibers 6 for optically coupling between the respective light receivers 21 and a spectral analyzing and light receiving unit 28, and the spectral analyzing and light receiving unit 28 made up of a spectral analyzing element 17 for spectrally analyzing the transmitted light 12 or the reflected light 14 and a light receiving element 18 such as a photodiode array for converting a light signal into an electric signal for each of wavelengths to thereby output a spectrum. In addition, the egg inspecting apparatus 1A includes an arithmetic unit 19 including the determining circuit 5 for performing an arithmetic process on the converted spectrum to determine if the egg having been inspected is a bloody egg that is to be rejected.

With this egg inspecting apparatus 1A, the white source light 11 is projected onto the egg E so as to illuminate the latter and the transmitted light 12 having passed through the egg E or the reflected light 14 reflected from the egg shell surface is received. Since the plural light receivers 21 are disposed around the egg E, an accurate reception of light is possible and, therefore, the inspecting accuracy can be increased. Also, in a manner substantially similar to the first embodiment, for each shell color the spectrum of the normal egg is measured and recorded. Thereafter, the egg shell colors are classified and, finally, the similarity between the spectral pattern of the egg and that of the normal egg recorded is assayed to thereby determine if the egg inspected is a bloody egg or not.

Figure 7:
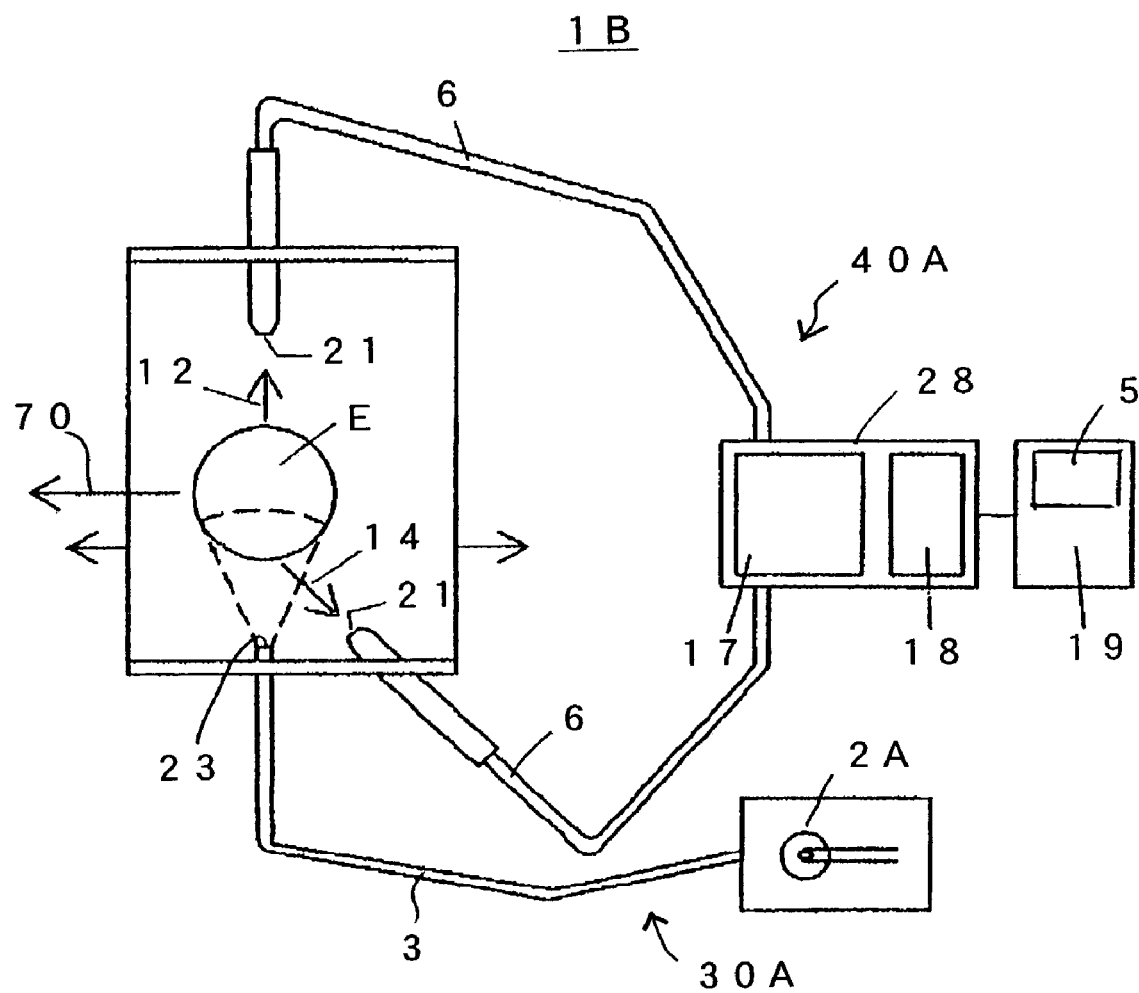
FIG. 7 is a schematic diagram showing a positioning mechanism for positioning the optical systems relative to each other, which is used in the egg inspecting apparatus of the present invention.

FIG. 7 illustrates a basic structure of a modified form of the egg inspecting apparatus according to the second preferred embodiment of the present invention. The egg inspecting apparatus 1B shown therein includes a transport mechanism 70 that makes it possible for detecting the bloody eggs while the eggs are transported, wherein a flexible optical fiber 3 is coupled with the halogen lamp 2A and the light receivers 21 and the spectral analyzing and light receiving unit 28 are coupled with each other by means of the flexible optical fibers 6. In this modified egg inspecting apparatus 1B, an optical system including respective light projecting ends 23 of the optical fibers 3 extending from the halogen lamp 2A and the light receivers 21 is caused to cyclically reciprocatedly moved over a predetermined range in a direction conforming to the direction of transport by the transport roller 70 shown in FIG. 7 while being synchronized with movement of the egg E at the inspecting site 54 of the automatic egg grading and packaging system 60 shown in FIG. 4. By so doing, the eggs can be highly accurately inspected while the optical systems are held stationary relative to the eggs being transported. The absorption spectrum of the pigment (protoporphyrin) contained in the egg shell exhibits a similar pattern in any of the spectrum of the transmitted light having passed through the egg and the spectrum of the reflected light.

Hereinafter, the present invention will be demonstrated by way of some specific examples. However, those examples are shown only for the purpose of illustration and are not intended to limit the scope of the present invention.

EXAMPLE 1

An egg inspecting apparatus 1 of the structure shown in FIG. 1 was assembled with the use of an automatic optical path selector 20 for selecting one of optical paths by causing a plane mirror 22 to undergo an angular movement, optical projecting fibers 3a each made up of a bundled configuration of 34,230 optical fiber strands of 50 micrometers in diameter, optical projecting fibers 3b each made up of a bundle configuration of 12,390 optical fiber strands of 50 micrometers in diameter and optical receiving fibers 6 each made up of a bundled configuration of 15 optical fiber strands of 200 micrometers in diameter. This egg inspecting apparatus 1 was incorporated in an egg grading and packaging system 60 of the structure shown in FIG. 4 and was then operated so that a white light 11 emitted from a light source 2 was guided selectively into the optical projecting fibers 3b by means of the automatic optical path selector 20 synchronized with operation of the six-row transport drive unit 57 for transporting eggs E in six rows so as to sequentially illuminate a transverse line of six eggs E1~E6 then held at an inspecting site. By automatically repeating this operation in an operatively associated fashion with the transport drive unit 57, transmitted light 12 having passed through the eggs one at a time was sequentially received by light receivers 21, then transmitted through the optical receiving fibers 6 to a spectral analyzing and light receiving unit 4 at which the transmitted light 12 was converted into an electric signal and a spectrum was eventually obtained.

In order to eliminate undesirable effects attributable to the thickness of the egg shell, the spectrum was normalized with respect to the light transmittance at the wavelength of 685 nm at which a component of the egg would virtually absorb no light. A secondary differential curve of this spectrum was then formulated and at a waveform of the absorption wavelength of 645 nm exhibited by the pigment contained in the egg shell, the color of the egg shell was classified into white color, rose-pink color and brown color. Also, as a measure indicative of similarity of spectral patterns between normal eggs for each shell color so classified, a threshold value of the correlation coefficient used to discriminate between a normal egg and a bloody egg was determined by a determining circuit 5 at the absorption wavelength region of 560 to 590 nm of hemoglobin. As shown in Table 1, when using this technique 3,413 eggs were examined, the rate of correctness at which the normal eggs were correctly identified was 100% in the case of the white-colored egg shell, 100% in the case of the rose-pink colored egg shell and 100% in the case of the brown colored egg shell and, on the other hand, the rate of correctness at which the bloody eggs were correctly identified was 94.5% in the case of the white-colored egg shell, 95.7% in the case of the rose-pink colored egg shell and 95.3% in the case of the brown colored egg shell. Thus, it has been ascertained that regardless of the shell colors, the bloody eggs could be inspected with high accuracy.

TABLE 1

| Shell Color | Quality | Number of Eggs Examined | Correctness Rate | Correctness Rate |
|---|---|---|---|---|
| White | Normal | 615 | 615 | 100.0% |
| Rose-pink | Normal | 306 | 306 | 100.0% |
| Brown | Normal | 551 | 551 | 100.0% |
| Sub-total | | 1,472 | 1,472 | 100.0% |
| White | Bloody | 1,259 | 1,190 | 94.5% |
| Rose-pink | Bloody | 256 | 245 | 95.7% |
| Brown | Bloody | 426 | 406 | 95.3% |
| Sub-total | | 1,941 | 1,841 | 94.8% |
| Total | | 3,413 | 3,313 | 97.1% |

EXAMPLE 2

An egg inspecting apparatus 1 of the structure shown in FIG. 3 was assembled with the use of an automatic optical path selector 20A for selecting one of optical paths by causing an optical head 25 to undergo an angular movement, optical projecting fibers 3a each made up of a bundled configuration of 34,230 optical fiber strands of 50 micrometers in diameter, optical projecting fibers 3b each made up of a bundled configuration of 12,390 optical fiber strands of 50 micrometers in diameter and optical receiving fibers 6 each made up of a bundled configuration of 12 optical fiber strands of 200 micrometers in diameter. This egg inspecting apparatus 1 was incorporated in an egg grading and packaging system 60 of the structure shown in FIG. 4 and the experiment was carried out in a manner similar to that in Example 1.

As shown in Table 2, when using this technique 1,876 eggs were examined, the rate of correctness at which the normal eggs were correctly identified was 100% in the case of the white-colored egg shell, 100% in the case of the rose-pink colored egg shell and 97.7% in the case of the brown colored egg shell and, on the other hand, the rate of correctness at which the bloody eggs were correctly identified was 94.5% in the case of the white-colored egg shell, 92.5% in the case of the rose-pink colored egg shell and 82.6% in the case of the brown colored egg shell. Thus, as compared with Example 1, the efficiency of utilization of the source light appears to be low in view of the fact that while the accuracy of examination of the bloody eggs of the white and rose-pink colored shells is high the accuracy of examination of the bloody eggs of the brown colored shell is relatively low.

TABLE 2

| Shell Color | Quality | Number of Eggs Examined | Correctness Rate | Correctness Rate |
|---|---|---|---|---|
| White | Normal | 555 | 555 | 100.0% |
| Rose-pink | Normal | 219 | 219 | 100.0% |
| Brown | Normal | 300 | 293 | 97.7% |
| | Sub-total | 1,074 | 1,067 | 99.3% |
| White | Bloody | 421 | 400 | 94.5% |
| Rose-pink | Bloody | 174 | 161 | 92.5% |
| Brown | Bloody | 207 | 171 | 82.6% |
| | Sub-total | 802 | 732 | 91.3% |
| | Total | 1,876 | 1,799 | 95.9% |

EXAMPLE 3

Using the egg inspecting apparatus of the structure shown in FIG. 6, a white light 11 emitted from a halogen lamp 2A of 100 watt rated output was used to illuminate white, rose-pink or brown colored normal eggs and light 12 transmitted through the normal eggs was spectrally analyzed and, using a system in which the transmitted light 12 is received by a photodiode array 18 capable of receiving light at intervals of 0.9 nm and converted into an electric signal, after the spectrum measurement, recording was made for each of the shell colors according to a command from an arithmetic unit 19. The spectrum of the egg E was measured in a similar manner and, in order to eliminate undesirable effects attributable to the thickness of the egg shell, the spectrum was normalized with respect to the light transmittance at the wavelength of 685 nm at which a component of the egg would virtually absorb no light. When a secondary differential curve of such spectrum was formulated, the shell color was classified to White Egg<0.0014≦Rose-pink Egg<0.0027≦Brown Egg according to a peak height at the wavelength of 645 nm at which the light absorption of the pigments of the egg shell is maximum. After the egg shells have been classified according to this classification method, the correlation between the spectral patterns of the normal eggs for each shell color at the wavelength region of 560 to 590 nm at which the light absorption by bloody eggs is remarkable was examined. As a result thereof, it has been found that the correlation coefficient ranged from 0.994 to 0.999 in the case of the white eggs, from 0.986 to 0.999 in the case of the rose-pink eggs and from 0.974 to 0.999 in the case of the brown eggs. Accordingly, the threshold value of the correlation coefficients for discriminating the eggs between normal eggs and bloody eggs for each shell color were set to 0.99 in the case of the white eggs, 0.98 in the case of the rose-pink eggs and 0.97 in the case of the brown eggs, and the correctness rates obtained when a total of 332 bloody eggs, including 126 white eggs, 103 rose-pink eggs and 103 brown eggs, were examined have shown 93% in the case of the white eggs, 99% in the case of the rose-pink eggs and 97% in the case of the brown eggs as shown in Table 3 below, with the average correctness rate being 96%.

TABLE 3

| Shell Color | Number of Eggs Examined | Correctness Rate | Correctness Rate |
|---|---|---|---|
| White | 126 | 117 | 93% |
| Rose-pink | 103 | 102 | 99% |
| Brown | 103 | 100 | 97% |
| Total | 332 | 319 | 96% |

EXAMPLE 4

In Example 3 the shell color was determined using the light 12 having been transmitted through the egg E while the latter was illuminated by the white light 11. However, in Example 4, light 14 reflected from an outer surface of the egg was used instead, and when after the spectrum of the reflected light 14 had been normalized in a manner similar to that in Example 3, the secondary differential curve of this spectrum was formulated, the shell color was classified to White Egg<0.0002≦Rose-pink Egg<0.0010≦Brown Egg according to a peak height at the wavelength of 645 nm at which the light absorption of the pigments of the egg shell is maximum. Using the same conditions as in Example 3 except for the classifying condition, a total of 175 bloody eggs, including 62 white eggs, 55 rose-pink eggs and 58 brown eggs, were examined.

As a result, the correctness rates obtained have shown 98% in the case of the white eggs, 96% in the case of the rose-pink eggs and 95% in the case of the brown eggs as shown in Table 4 below, with the average correctness rate being 97%.

TABLE 4

| Shell Color | Number of Eggs Examined | Correctness Rate | Correctness Rate |
|---|---|---|---|
| White | 62 | 61 | 98% |
| Rose-pink | 55 | 53 | 96% |
| Brown | 58 | 55 | 95% |
| Total | 175 | 169 | 97% |

EXAMPLE 5

The egg inspecting apparatus used in Example 3 was incorporated in the automatic grading and packaging system 60 for the eggs E shown in FIG. 5 and, as shown in FIG. 7, the flexible optical fiber 3 was coupled with the halogen lamp 2A and the flexible optical fibers 6 were coupled between the light receivers 21 and a spectral analyzing and light receiving unit 28. Then, a light projecting end 23 of the optical fiber 3 extending from the halogen lamp 2A and the light receivers 21 were cyclically reciprocated over a predetermined range of 50 mm in a direction conforming to the direction of transport of a transport roller 70 in synchronism with movement of the eggs moving at a speed of 90 mm per second past an inspecting site 54 of the grading and packaging system 60, to thereby hold the eggs stationary relative to the inspecting optics. When in this condition the secondary differential curve related to the spectrum of the normal eggs was formulated in a manner similar to that in Example 3, the shell color was classified to White Egg<0.0014≦Rose-pink Egg<0.0027≦Brown Egg according to a peak height at the wavelength of 645 nm at which the light absorption of the pigments of the egg shell is maximum. When a total of 370 bloody eggs, including 150 white eggs, 113 rose-pink eggs and 107 brown eggs, were examined, the correctness rates were obtained, indicating 95% in the case of the white eggs, 96% in the case of the rose-pink eggs and 93% in the case of the brown eggs as shown in Table 5 below, with the average correctness rate being 95%. As a result of these egg inspection information having been transmitted to a defective egg rejecting unit 58 according to a command generated by a system control unit 50 installed in the automatic grading and packaging system 60, the bloody eggs were rejected with high accuracy.

TABLE 5

| Shell Color | Number of Eggs Examined | Correctness Rate | Correctness Rate |
|---|---|---|---|
| White | 150 | 143 | 95% |
| Rose-pink | 113 | 109 | 96% |
| Brown | 107 | 100 | 93% |
| Total | 370 | 352 | 95% |

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. An egg inspecting apparatus which comprises:
an optical path switching and projecting assembly for automatically selecting one of a plurality of optical paths through which a white source light emitted from a common light source is guided and also for sequentially projecting the white source light from the associated optical paths onto eggs held at respective positions;
a spectrum converting assembly for spectrally analyzing light which has passed through each of the eggs and converting it into a spectrum; and
a determining circuit for determining whether the egg is a normal egg or a bloody egg by using the spectrum so converted.

2. The egg inspecting apparatus as claimed in claim 1, wherein the optical path switching and projecting means includes an automatic optical path selector for sequentially guiding the white source light into one of the optical paths by means of a drive of a rotational angle control motor.

3. The egg inspecting apparatus as claimed in claim 1, wherein each of the optical paths is defined by an optical fiber.

4. The egg inspecting apparatus as claimed in claim 1, wherein the spectrum converting assembly includes a light receiver for receiving the light which has been transmitted through one of the eggs, and a spectral analyzing and light receiving unit for spectrally analyzing the transmitted light and for converting a light signal into an electric signal to thereby output a spectrum, said light receiver and said spectral analyzing and light receiving unit being coupled with each other through an optical fiber, and
wherein spectra of the eggs are sequentially measured by transmitting the light, having passed through the eggs and subsequently received by the light receiver, to the spectral analyzing and light receiving unit through the optical fiber.

5. The egg inspecting apparatus as claimed in claim 4, wherein a center axis of the light receiver for receiving the light transmitted through the egg is inclined relative to a center axis of the source light used to illuminate the egg such that for avoiding an erroneous operation of a light receiving element of the spectral analyzing and light receiving unit in the absence of the egg at an inspecting site, the light receiver will not receive directly the source light of an intensity exceptionally higher than the intensity of the transmitted light.

6. The egg inspecting apparatus as claimed in claim 1, wherein the determining circuit is operable to determine if the egg is a normal egg or a bloody egg, by classifying an egg shell color by utilization of a spectrum of light reflected from an outer surface of an egg shell as a result of illumination of the egg with the source light and then utilizing the spectrum of the transmitted light having passed through the egg.

7. An egg inspecting method which comprises the steps of:
automatically selecting one of a plurality of optical paths through which a white source light emitted from a common light source is guided to thereby project sequentially the white source light from the associated optical paths onto eggs held at respective positions;
spectrally analyzing light which has passed through each of the eggs to thereby convert it into a spectrum; and
determining whether the egg is a normal egg or a bloody egg by using the spectrum so converted.

8. The egg inspecting method as claimed in claim 7, wherein the step of determining whether the egg is a normal egg or a bloody egg is such that after the intensity of a spectrum of the light that has been transmitted through each egg has been divided by the intensity of a spectrum of the source light emitted from the light source and such divided intensity has been converted into a light transmittance, the spectrum of the transmitted light is normalized by the light transmittance at the wavelength of light little absorbed by a component of the respective egg and, then, a secondary differential curve of the spectrum is formulated to classify the egg shell color according to a peak intensity of a spectral absorption band exhibited by protoporphyrin, which is a pigment of an egg shell, and thereafter at a different spectral absorption band exhibited by hemoglobins contained in the bloody egg, in reference to a similarity between a spectral pattern of the egg and a spectral pattern of a normal egg having no blood, whether the egg inspected is a bloody egg or not is determined for each of the classified egg shell colors.

9. An egg grading and packaging system including the egg inspecting apparatus as defined in claim 1, which apparatus has loaded therein a computer-executable program to thereby render the system to have a capability of rejecting bloody eggs by automatically inspecting presence or absence of those bloody eggs while the eggs are transported successively.

10. An egg inspecting apparatus which comprises:
   a projecting assembly for projecting a white light, emitted from a light source, onto eggs;
   a spectrum converting assembly including a light receiver for receiving light transmitted through each of the eggs and a spectral analyzing and light receiving unit for spectrally analyzing the transmitted light and converting a light signal into an electric signal to provide a spectrum; and
   a determining circuit for measuring the spectrum of the transmitted light having passed through the egg, after a spectrum of light transmitted through a normal egg having no blood contained therein has been measured and recorded for each of egg shell colors, and for determining at a plurality of wavelengths covering the spectral absorption band from 560 nm to 590 nm exhibited by hemoglobin, after the egg shell colors have been classified according to an light absorbency exhibited by a pigment of an egg shell or a spectrum of light reflected from an outer shell surface of the egg, if the egg being inspected is a bloody egg in dependence on a similarity to a spectral pattern exhibited by the normal egg.

11. The egg inspecting apparatus as claimed in claim 10, further comprising:
   a transport mechanism enabling the eggs to be successively inspected while the eggs are being transported;
   a first flexible optical fiber coupled with the light source; and
   a second flexible optical fiber coupling between the light receiver and the spectral analyzing and light receiving element; and
   whereby with an operating condition in which the eggs, a light projecting end of the first optical fiber extending from the light source and the light receiver are held stationary relative to each other while moving corresponding to the movement of the egg over a predetermined range in a direction conforming to the direction in which the eggs are successively transported by the transport mechanism, the eggs are illuminated by the source light while only the light transmitted through the egg is received by the light receiver.

12. The egg inspecting apparatus as claimed in claim 10, wherein the determining circuit classifies the egg shell colors according to a peak intensity of the pigment in a secondary differential curve of the spectrum of the transmitted light through the egg after a light absorbency in a wavelength region in which protoporphyrin, which is a pigment of an egg shell, does not absorb has been normalized.

13. The egg inspecting apparatus as claimed in claim 10, wherein the determining circuit is operable to determine if the egg is a bloody egg, by assaying with a correlation coefficient a similarity between a spectral pattern exhibited by the transmitted light through the egg and the spectral pattern exhibited by the transmitted light through the normal egg in a wavelength region in which blood hemoglobins exhibit light absorption.

14. The egg inspecting apparatus as claimed in claim 11, wherein the light receiver is employed in a plural number and disposed around the egg so that the light transmitted through or reflected from the egg are received by the plural light receivers and are subsequently transmitted to the spectral analyzing and light receiving unit through the associated optical fibers.

15. An egg inspecting method which comprises the steps of:
   projecting a white light, emitted from a light source, onto eggs;
   receiving light transmitted through each of the eggs and spectrally analyzing the transmitted light and converting a light signal into an electric signal to provide a spectrum; and
   measuring a spectrum of the transmitted light having passed through the egg, after a spectrum of light transmitted through a normal egg having no blood contained therein has been measured and recorded for each of egg shell colors and, subsequently, determining at a plurality of wavelengths covering the spectral absorption band from 560 nm to 590 nm exhibited by hemoglobin, after the egg shell colors have been classified according to an light absorbency exhibited by a pigment of an egg shell or a spectrum of light reflected from an outer shell surface of the egg, if the egg being inspected is a bloody egg in dependence on a similarity to a spectral pattern exhibited by the normal egg.

16. An egg inspecting apparatus which comprises:
   a projecting assembly for projecting a white light, emitted from a light source, onto eggs;
   a spectrum converting assembly including a light receiver for receiving light transmitted through each of the eggs and a spectral analyzing and light receiving unit for spectrally analyzing the transmitted light and converting a light signal into an electric signal to provide a spectrum; and
   a determining circuit for measuring the spectrum of the transmitted light having passed through the egg, after a spectrum of light transmitted through a normal egg having no blood contained therein has been measured and recorded for each of egg shell colors, and for determining at the entire spectral absorption band exhibited by hemoglobin, after the egg shell colors have been classified according to a spectrum of light reflected from an outer shell surface of the egg, if the egg being inspected is a bloody egg in dependence on a similarity to continuous spectral pattern exhibited by the normal egg.

* * * * *